United States Patent [19]

Slater

[11] Patent Number: 5,203,785
[45] Date of Patent: Apr. 20, 1993

[54] LAPAROSCOPIC HOOK SCISSORS

[75] Inventor: Charles R. Slater, Fort Lauderdale, Fla.

[73] Assignee: Symbrosis Corporation, Miami, Fla.

[21] Appl. No.: 780,013

[22] Filed: Oct. 21, 1991

Related U.S. Application Data

[63] Continuation-in-part of Ser. No. 521,766, May 10, 1990, and a continuation-in-part of Ser. No. 680,392, Apr. 4, 1991.

[51] Int. Cl.⁵ .............................................. A61B 17/00
[52] U.S. Cl. .................................... 606/205; 606/207; 606/170; 606/174; 128/751; 30/131; 227/19
[58] Field of Search .................. 128/749, 751; 30/250, 30/251, 155, 335, 131, 134; 606/205, 206, 207, 208, 167, 170, 174, 138; 403/279, 284, 282; 254/28; 227/19, 180, 175

[56] References Cited

U.S. PATENT DOCUMENTS

| | | | |
|---|---|---|---|
| 1,507,738 | 9/1924 | Johnson | 254/28 |
| 2,033,050 | 3/1936 | Pankonia | 254/28 |
| 2,618,268 | 11/1952 | English | 227/19 |
| 2,853,074 | 9/1958 | Olson | 227/19 |
| 3,241,814 | 3/1966 | Forte | 254/28 |
| 3,581,551 | 6/1971 | Wilkinson | 227/19 |
| 3,895,636 | 7/1975 | Schmidt | 606/174 |
| 4,569,346 | 2/1986 | Poirier | 606/174 |
| 4,637,538 | 6/1987 | Wagner | 254/28 |
| 4,760,848 | 8/1988 | Hosson | 606/174 |
| 4,776,567 | 10/1988 | Strickland | 254/28 |
| 4,950,273 | 8/1990 | Briggs | 606/174 |
| 4,977,900 | 12/1990 | Fehling et al. | 128/751 |
| 5,009,657 | 4/1991 | Cotey et al. | 606/167 |

Primary Examiner—Francis Jaworski
Assistant Examiner—Scott R. Akers

[57] ABSTRACT

Hook scissors end effectors are provided for a laparoscopic instrument. The hook scissors end effectors generally comprise first and second blades, with at least one of the blades pivotally engaging the laparoscopic instrument. Each blade comprises an elongate straight blade member with an integral transverse hook element at the distal end of the blade member. The hook elements each extend towards the other blade member and each hook element is offset from its blade member so that a narrow recess is provided between opposing first and second hook members upon closing of the first and second blade members. The elongate straight blade members provide a straight scissors cutting action therebetween so that the contiguously adjacent portions of the blade members gradually come together in a continuous bearing contact to effect a cutting action. While the hook elements at the distal ends of the blades effectively provide a hook which contains the object to be severed, the distal portions of the blade members do not establish contact with each other until the cutting action reaches the distal portion of the scissors.

16 Claims, 5 Drawing Sheets

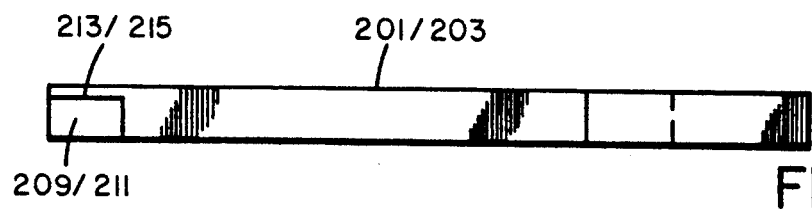
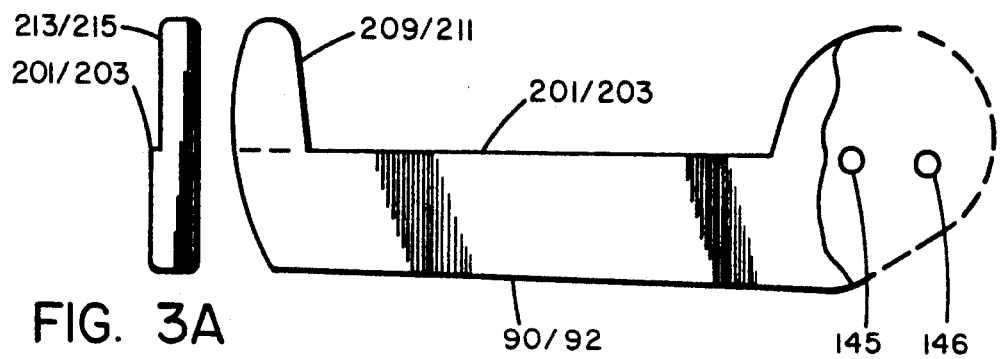
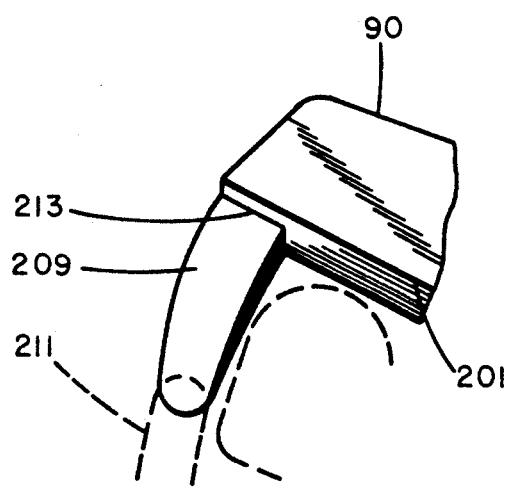

LAPAROSCOPIC HOOK SCISSORS

This is a continuation-in-part of U.S. Ser. No. 07/521,766 filed May 10, 1990 and U.S. Ser. No. 07/680,392 filed Apr. 4, 1991 which are hereby incorporated by reference herein in their entirety.

BACKGROUND OF THE INVENTION

The present invention broadly relates to laparoscopic surgical instruments. More particularly, the invention relates to surgical instruments having end effectors in the form of scissors useful in a laparoscopy procedure which involves the lifting of a structure away from surrounding tissue prior to severing the structure by scissoring action.

The laparoscopy procedure has recently become a widely practiced surgical procedure. A laparoscopy procedure typically involves incising through the naval and through the abdominal wall for viewing and/or operating on the ovaries, uterus, gall bladder, bowels, appendix, although more recently, incisions and insertion of trocar tubes have been made in different areas of the abdomen and even in the chest cavity. Typically, trocars are utilized for creating the incisions. Trocar tubes are left in plane in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Previous to the present invention, laparoscopic tools have utilized scissor end effectors of the hook type which have hooked (scooped) blades for ensuring that the tips of the cutting blades come together before cutting action starts. The problem with the laparoscopic hooked scissors of the art is that the structure to be cut (e.g., a duct, vein, tendon, etc.) often gets trapped between the blades in such a manner that cutting is difficult and/or that the cut made is jagged (i.e., not clean). The applicants have determined that a primary reason for the difficulty in cutting with the hooked scissors of the art is that clean cutting requires that the cutting blades be forced into contact at preferably a single moving cutting point. Simple scissors are built in such a fashion that the blades are forced into contact at a single point by a torque acting from their pivoting point and arising from elastic deformation of the blades or some other resilient means at or near the pivoting point. The hook scissors of the art have been designed to have two cutting points where the edges of the scooped blades touch. The difficulty with this design is that it is difficult, if not impossible, to fabricate such scissors so that the torque acting from their pivot point causes both desired cutting points to be forced together. Indeed, such scissors are usually hand built with a minimum of resilience in their construction and fitted together with minimum operating clearance at the pivot point so that the two blades, while not being actually forced into contact at either of the intended cutting points, close with very little clearance. Such an arrangement, even when executed with skill, will often fail to cut materials with a fibrous or elastic nature, thereby causing the blades to separate (i.e., a lateral gap will form). Also, the action of the hook scissors of the art is such that the two cutting points start at the inner and outer ends of the blades and move to meet at the middle of the cutting area. This closing action causes fibrous and elastic material to bunch in the scissors, resulting in further force pushing the blades apart and inhibiting their cutting actions.

SUMMARY OF THE INVENTION

It is therefore and object of the invention to provide a hook scissors for laparoscopic instruments which is constructed to provide only a single moving point of contact between blades when actuated.

Another object of the invention is to provide laparoscopic hook scissors having hook elements at the distal ends of the blades, which hook elements do not contact each other during cutting action.

In accord with the objects of the invention, a hook scissors end effector device is provided for a laparoscopic instrument. The hook scissors end effectors generally comprise first and second blades, with at least one of the blades being pivotally engaged, and each blade comprising an elongate straight blade member with an integral transverse hook element at the distal end of the blade member. The hook elements each extend towards the other blade member and each hook element is offset from its blade member so that a narrow recess is provided between opposing first and second hook members upon closing of the first and second blade members. The elongate straight blade members provide a straight scissors cutting action therebetween so that the contiguously adjacent portions of the blade members gradually come together in a continuous bearing contact to effect a cutting action. While the hook elements at the distal ends of the blades effectively provide a hook which contains the object to be severed, the distal portions of the blade members do not establish contact with each other until the cutting action reaches the distal portion of the scissors.

A better understanding of the disposable laparoscopic hook scissors instrument of the invention, and additional advantages and objects of the invention will become apparent to those skilled in the art upon reference to the detailed description and accompanying drawings.

BRIEF DESCRIPTION OF THE DRAWINGS

FIG. 1a is a cross sectional view through the laparoscopic instrument of FIG. 1 at the indicated location;

FIGS. 3, 3(A) and 3(B) are enlarged elevation, plan and side views of one of the blades of the device of FIG. 2;

FIG. 5 is an enlarged fragmentary perspective view of a distal portion of a blade member of FIG. 2.

DETAILED DESCRIPTION OF THE PREFERRED EMBODIMENT

Figure 1:
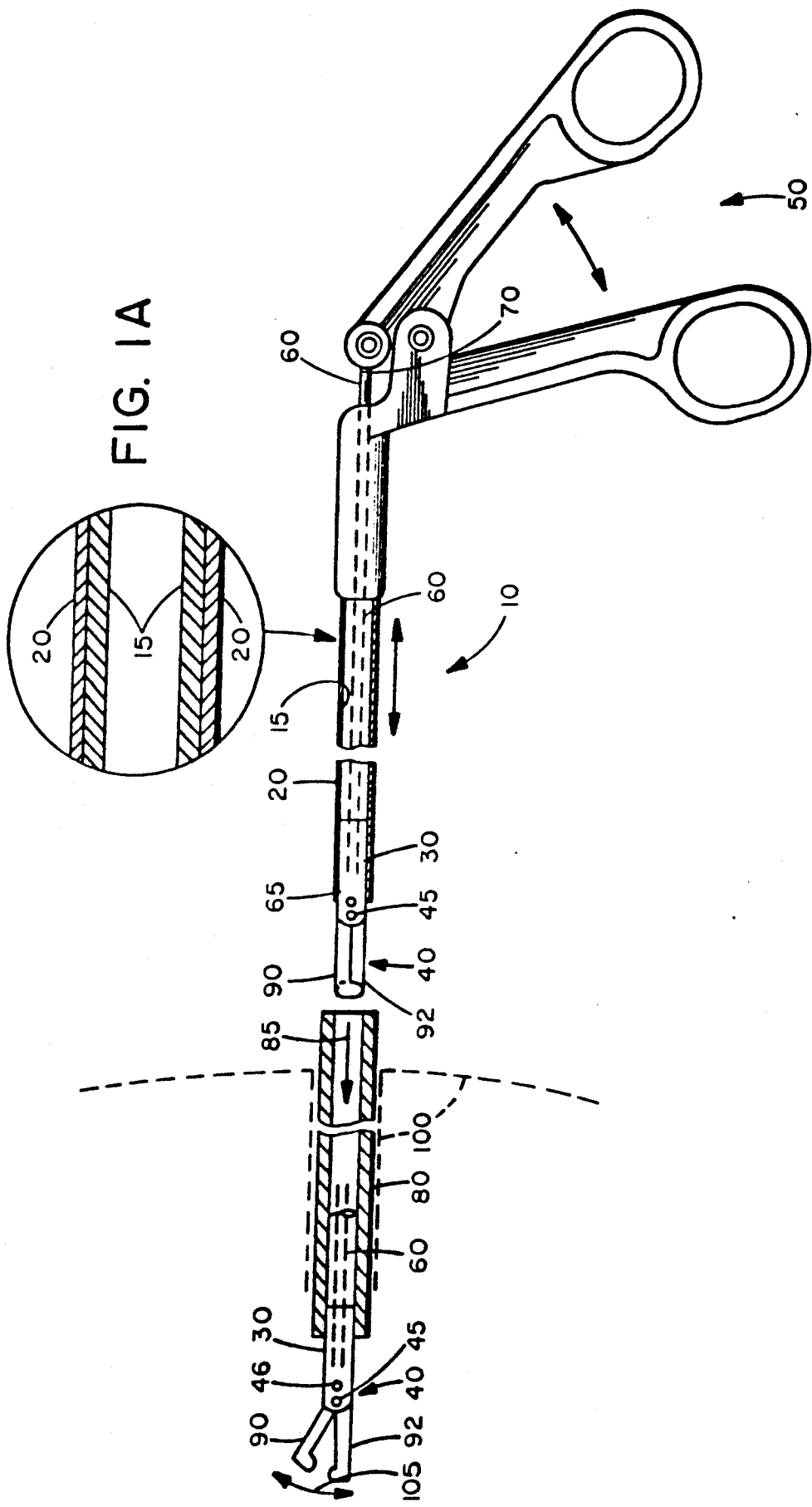
FIG. 1 is a side elevation view, partly in section, of a disposable laparoscopic instrument prior to insertion into a trocar tube, and, in partial phantom format, after insertion into a trocar tube.

With reference to FIG. 1, (and FIG. 1A), a disposable laparoscopic surgical instrument is indicated at 10. The disposable laparoscopic surgical instrument 10 includes an aluminum tube 15 surrounded by a peripheral insulating shrink wrap layer of plastic 20, a clevis means 30, hook scissors end effectors 40, actuating means 50, and a push rod 60. The clevis means 30 is preferably a separately formed aluminum piece which fixedly engages aluminum tube 15. The clevis 30 also engages the manipulating members 90, 92 of the end effector 40. Member 90 is pivotally engaged to clevis 30 at pivot pin 45 and member 92 is fixedly engaged to the clevis 30 at pin 45 and post 46. End effector 40 is preferably formed of a cobalt base alloy, although it can be formed of other materials such as, e.g., stainless steel, if desired. The push rod 60, which is preferably formed of stainless steel, is engaged at its distal end 65 to the end effector 40, as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the blades 90, 92 of the end effector 40, in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, one or both of the blades 90, 92 can be opened and closed as indicated at 105 by reciprocal motion of push rod 60 which results from operation of the manual actuating means 50. As is discussed in more detail in Ser. No. 07/680,392, the clevis effectively helps to translate the reciprocal motion of the push rod 60 into the end effector means action indicated at 105.

Additional detail regarding the laparoscopy instrument 10 may be obtained by reference to previously incorporated U.S. Ser. No. 07/680,392. It is noted, however, that the preferred embodiment of the hook scissors is a single acting tool with one of the end effector blades stationary.

Figure 2:
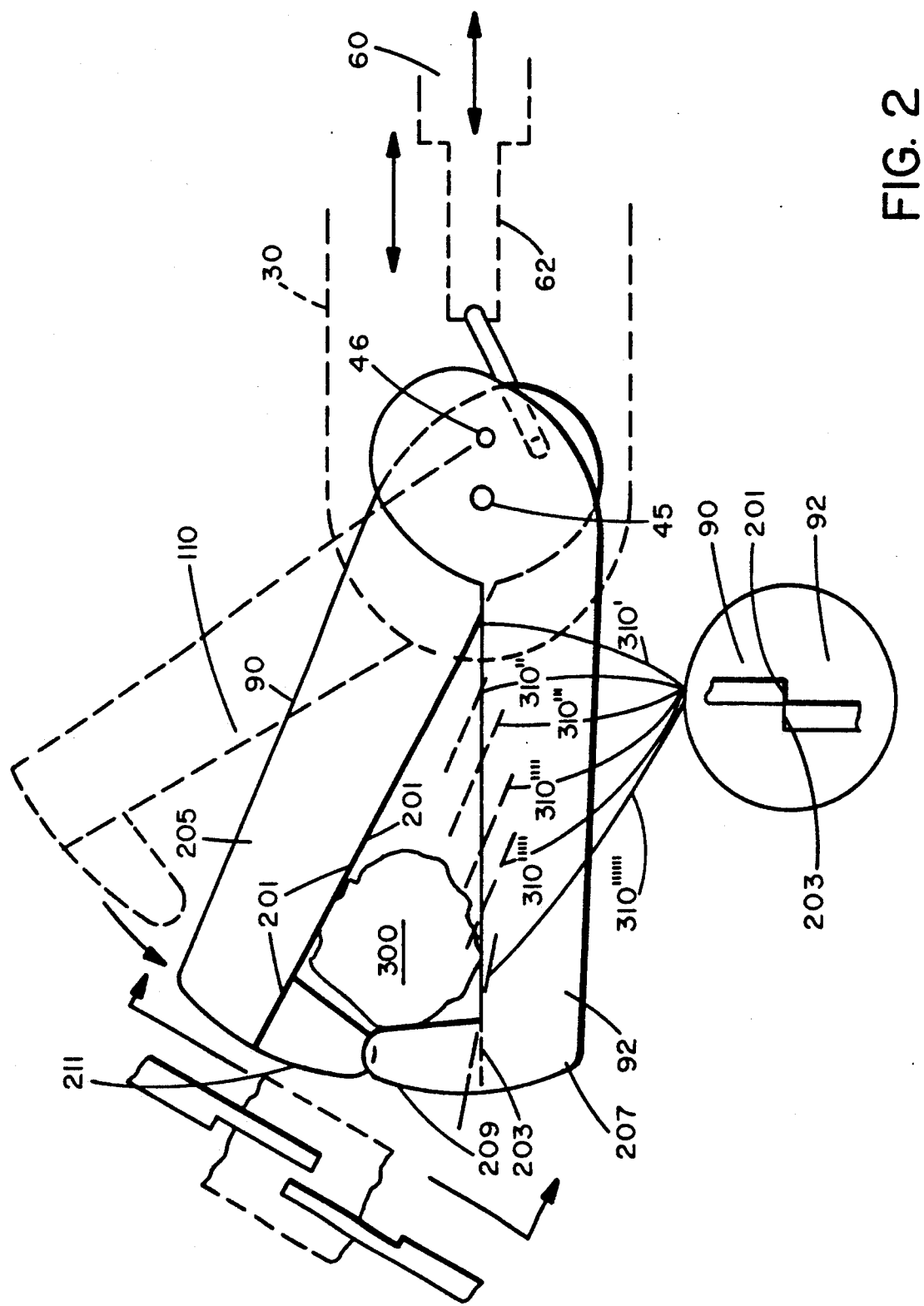
FIG. 2 is an enlarged side elevation view, of the hook scissors end effectors of the invention in an open position.

With reference to FIG. 2, the hook scissors end effector of the present invention is shown at 110 in an open position having a pivotally rotatable blade member 90 which is rotatable about pivot pin 45 of clevis 30 as more fully described hereinafter. Blade member 92 preferably also engages the pivot pin 45. However, because blade member 92 is provided with a post 46 which engages a hole 46' in clevis 30, blade member 92 is fixed in position with respect to clevis 30. Blade members 90, 92 are held in a tight bearing contact by pivot pin 45 which extends through holes 145 of the blade members and which engages the clevis 30. Each blade member 90, 92 has a respective straight cutting edge 201, 203 which extends along blades 90, 92 to their terminal distal portions 205, 207 remote from the pivotal engagement at 45.

Figure 4:
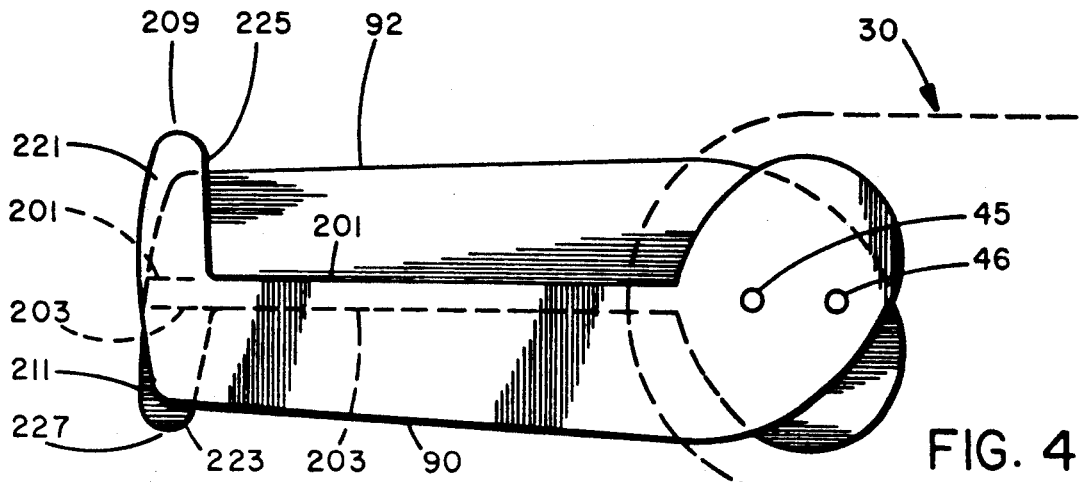
FIGS. 4, 4(A) and 4(B) are enlarged elevation, plan and front elevation views of the device of FIG. 2 in the closed position.
Figure 4A:
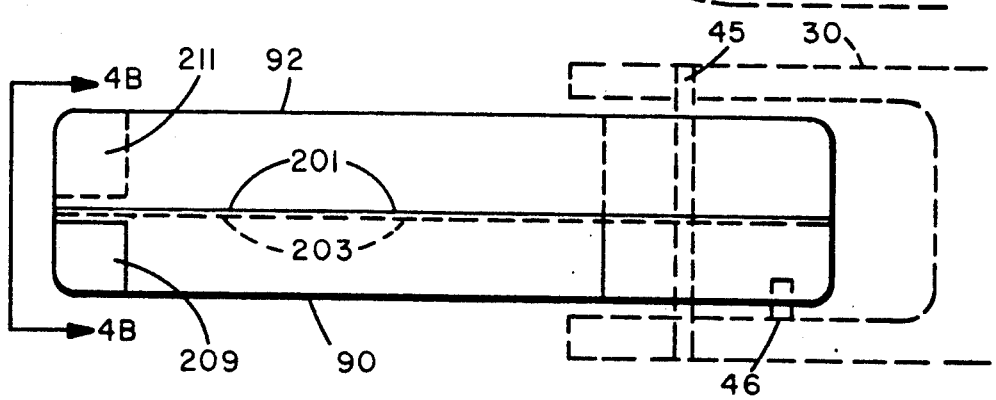
Figure 4B:
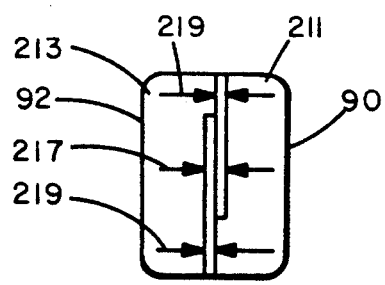

The hook scissors end effectors of FIG. 2 are comprised of substantially identical blade members 90, 92 (minor differences such as the provision of a projection or post 46 for insertion into a hole 46' in the clevis, and the elimination of a hole 146 for a connecting means being provided where one blade member is fixed). As seen in FIG. 3, each elongate straight blade member 90, 92 has a transverse integral hook element 209, 211. The hook elements 209, 211 extend toward each other in the open position of FIG. 2 and are offset from their respective blade members as indicated at 213, 215 of FIG. 3 to provide a narrow recess 217 (FIG. 4B) between the opposing hook elements when the blade members are closing or in the closed position. An even narrower recess 219 is formed between each blade member 90, 92 and the adjacent hook member 209, 211 of the other blade member 90, 92 when the blade members are closing. As shown in FIG. 4, the terminal portions 221, 223 of the hook elements 209, 211 of blade members 90, 92 are preferably rounded at 225, 227, and the edges of hook elements 209, 211 are preferably blunt, i.e. not sharpened as compared to blade edges 201, 203 which are sharpened and in close bearing contact.

In use, blade 90 can be opened relative to blade 92 as shown in phantom in FIG. 2, such that a tissue, vein, duct, or other object 300 can be gently grabbed by the hook element 209 of blade 92. By closing blade 90 relative to blade 92 as shown in FIG. 2, object 300 is encompassed by the non-sharpened, non-contacting, blunt edged, parallel, opposed hook elements 209, 211. With the object 300 so encompassed (or with hook element 209 grabbing the object as in the case of a vein or other small object), the object can be pulled to a location where positive identification by imaging or other equipment is achieved. When the identity of the encompassed object is identified, and cutting is desired, the cutting operation along cutting edges 201, 203 proceeds by pivotal movement of blade member 90. With the device of the present invention, a clean cut is provided by cutting edges 201, 203 as blade member 90 and 92 contact with each other along a continuously moving bearing contact point 310'-310''-310'''-310''''-310'''''-310'''''', thereby avoiding entrapment of tissue between laterally displaced blade members. Also, since cutting proceeds from one end only, the accidental cutting of an object which can happen in the prior art hook scissors is avoided during the procedure of grabbing the object, as the opposed hook elements 209, 211 do not act to cut.

Typical dimensions for the hook scissors end effectors in accordance with the present invention are as follows for a device made of stainless steel:

| | |
|---|---|
| Cutting blade (201, 203) length from pivot point to hook: | .5 in. |
| Cutting blade (201, 203) thickness: | .03 in. |
| Length of hook element (213, 215): | .07 in. |
| Thickness of hook element (213, 215): | .029 in. |
| Width of recess 217: | .002 in. |
| Width of recess 219: | .001 in. |

Figure 6:
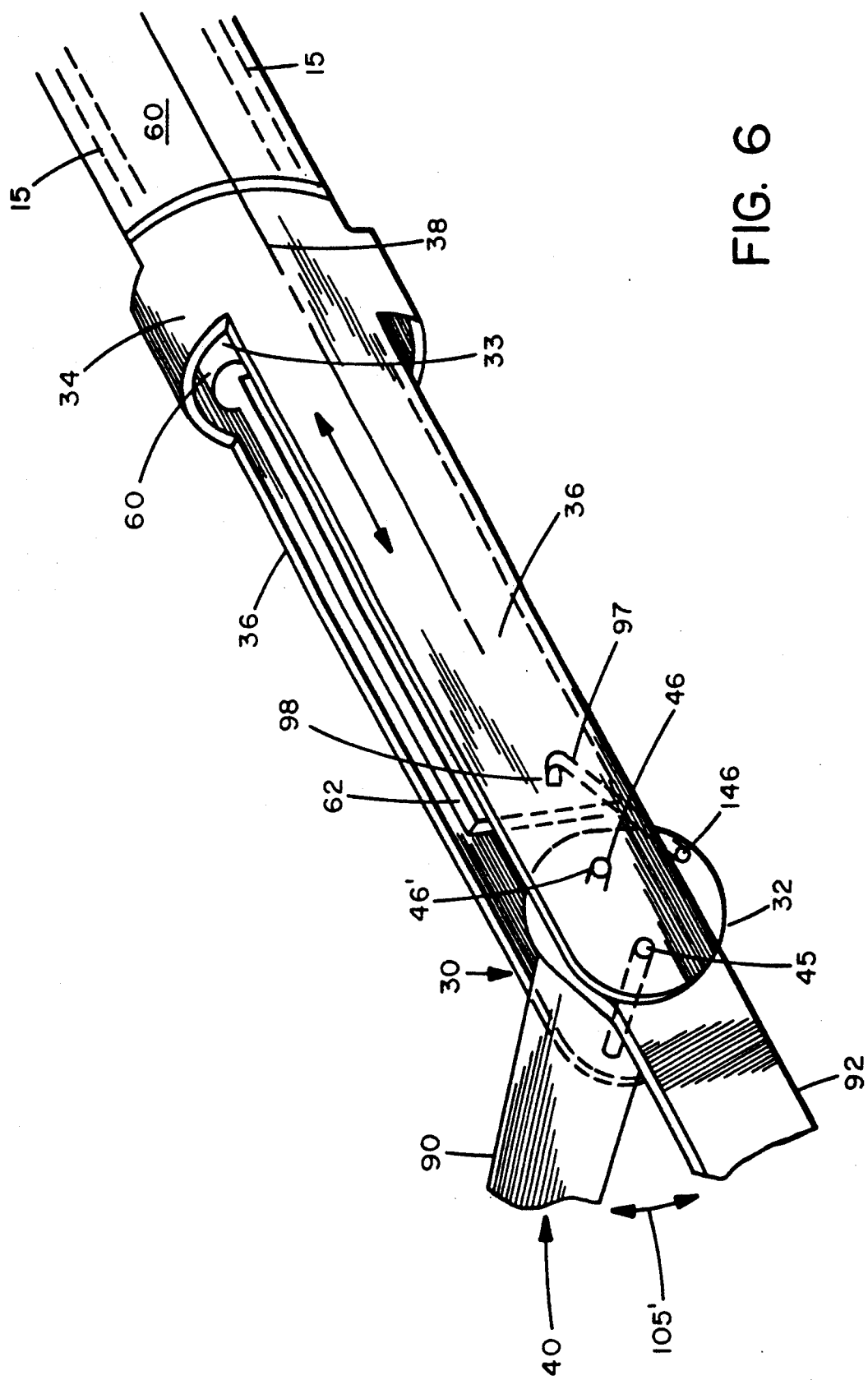
FIG. 6 is a perspective view of the clevis element usable with the hook scissors device of FIG. 2.

Turning to the perspective view of FIG. 6, a preferred configuration of the clevis 30 for use with the present invention is seen. The clevis has a knurled rod-like proximal portion 15 for mating with the end of the aluminum tube 15, and a pivot-supporting U-shaped distal portion 32 for holding the end effector means 40 comprising members 90, 92. The proximal portion 34 of the clevis is preferably hollow, as indicated at 33, to permit the push rod 60, with its flattened terminal portion 62 to extend therethrough. The distal portion 32 of the clevis 30 is provided with a pivot pin 45 which is generally perpendicular, i.e. transverse, to the legs 36 of the clevis. In addition, where a single acting end effector is provided, one of the legs of clevis 30 is provided with a hole 46'. The fixed end effector blade 92 of the single acting instrument is provided with a transverse or lateral protrusion 46 which extends into hole 46'. As a result, fixed blade 92 is fixed relative to the clevis 30 by engagement of protrusion 46 in hole 46' and by engagement of hole 145 at pivot pin 45. On the other hand, the pivoting blade member 90 is engaged at through hole 146 by a metal link member 97 to push rod 60 which is engaged to link member 97 at through hole 98. Upon actuation of push rod 60, blade member 90 moves pivotally around pin 45 to provide the scissor action indicated at 105' while blade member 92 remains stationary. Double acting hook scissors are easily obtained by eliminating the protrusion 46 and hole 46', and by substituting an additional metal link member as is disclosed in previously incorporated U.S. Ser. No. 07/680,392.

There has been described and illustrated herein laparoscopic hook scissors. While particular embodiments of the invention have been described, it is not intended that the invention be limited exactly thereto, as it is intended that the invention be as broad in scope as the art will allow. Thus, while a scissors having a particular single pivot actuating means was described, it will be appreciated that different arrangements such as described in copending U.S. Pat. No. 5,171,258 can be utilized to provide a scissors with additional cutting leverage. Also, while a scissors with particular dimensions and comprised of particular materials was described, it will be appreciated that other materials could be utilized and that the scissors can have different dimensions. Therefore, it will be apparent to those skilled in the art that other changes and modifications may be made to the invention as described in the specification without departing from the spirit and scope of the invention as so claimed.

What is claimed is:

1. In a surgical hook scissors suitable for insertion through a trocar tube and having an outer tube having a longitudinal axis, first and second end effector scissor blade means, pivot means coupled to and transverse said outer tube, and an actuating means extending through said outer tube and coupled to at least said said first end effector scissor blade means, an improvement comprising:
   a) said first and second end effector scissor blade means laterally offset from each other, said first and second end effector scissor blade means having respective first and second elongate straight blade members having respective first and second inside cutting edges with respective proximal and distal ends, said first blade member having a through-hole in a proximal portion of said first blade member for pivotally engaging said pivot means, wherein, when said pivotally engaging first blade member pivots towards a closing position, said inside cutting edge of said first straight elongate straight blade member engages said inside cutting edge of said second elongate straight blade member in a bearing contact starting at a point proximal said distal ends of said inside cutting edges and moving distally therefrom to effect a cutting action;
   b) a first hook element integral with said first blade member at a distal portion of said first blade member, said first hook element laterally offset relative to and indented from said first cutting edge of said first blade member and extending away from said first blade member and toward said second blade member;
   c) a second hook element integral with said second blade member at a distal portion of said second blade member, said second hook element laterally offset relative to and indented from said second cutting edge of said second blade member and extending away from said second blade member and toward said first blade member, wherein a narrow recess is provided between said first and second hook members upon closing of said first and second blade members.

2. In a surgical hook scissors according to claim 1, wherein:
said first and second hook elements are sufficiently indented respectively from said first and second inside cutting edges of said first and second blade members so that a narrow recess is provided between each blade member and the adjacent hook element of the other blade member when the blade members are in a fully closed position with said distal ends of said cutting edges contacting each other.

3. In a surgical hook scissors according to claim 2, wherein:
said first and second blade members are substantially identical.

4. In a surgical hook scissors having a clevis means with said pivot means, according to claim 1, wherein:
said second blade member is fixedly engaged to said clevis means.

5. In a surgical hook scissors according to claim 4, wherein:
said second blade member fixedly engaged to said clevis means includes a lateral protrusion extending from a proximal portion of fixedly engaged second blade member, said lateral protrusion for engagement with a hole in said clevis means.

6. In a surgical hook scissors where said actuation means includes a push rod and connecting means for coupling the push rod to at least said first end effector scissor blade means, according to claim 1, wherein:
said first blade member has a second through-hole for receiving said connecting means.

7. In a surgical hook scissors where said actuation means includes a push rod and connecting means for coupling the push rod to at least said first end effector scissor blade means, according to claim 2, wherein:
said first blade member has a second through-hole for receiving said connecting means.

8. In a surgical hook scissors where said actuation means includes a push rod and connecting means for coupling the push rod to said first and second end effector scissor blade means, according to claim 1, wherein:
said first and second blade members each have a second through-hole for receiving said connecting means.

9. In a surgical hook scissors according to claim 1, wherein:
each of said first and second hook elements has a smooth rounded terminal portion remote from said respective first and second blade members with which they are integral.

10. A surgical hook scissors suitable for insertion through a trocar tube, comprising:
   a) a hollow tube having a distal end and a proximal end;
   b) a clevis means mechanically coupled to said distal end of said tube;
   c) first and second end effector scissor blade means laterally offset from each other, said first and second end effector scissor blade means having respective first and second elongate straight blade members having respective first and second inside cutting edges, said first blade member having a first through-hole in a proximal portion of said first blade member for pivotally engaging said clevis means, said first end effector blade means having a first hook element integral with said first blade member at a distal portion of said first blade member, said first hook element laterally offset relative to and indented from said first inside cutting edge of said first blade member and extending away from said first blade member and toward said second blade member, and said second end effector blade means having a second hook element integral with said second blade member at a distal portion of said second blade member, said second hook element laterally offset relative to and indented from said second inside cutting edge of said second blade member and extending away from said second blade member, and toward said first blade members;
   d) a rod means extending at least partially through said hollow tube and having a first end and a second end, said rod means being coupled to said pivotally engaged first blade member; and
   e) actuating means engaged to said second end of said rod for imparting reciprocal motion to said rod relative to said tube which is translated to pivotal motion of said pivotally engaged first blade member.

11. A surgical hook scissors according to claim 10, wherein;
   said pivotally engaging first blade member has a second through-hole in said proximal portion of said first blade member, sand said surgical hook scissors further comprises,
   a connecting means extending through said second through-hole and coupling said first end of said rod with said pivotally engaging first blade member.

12. A surgical hook scissors according to claim 10, wherein:
   said first and second hook elements are sufficiently indented from respective inside cutting edges of said first and second blade members so that a narrow recess is provided between said first and second hook members upon closing of said first and second blade members, and so that a narrow recess is provided between each blade member and adjacent hook element of the other blade member when the blade members are in a fully closed position with said distal ends of said blade members contacting each other.

13. A surgical hook scissors according to claim 12, wherein:
   said second member is fixedly engaged to said clevis means.

14. A surgical hook scissors according to claim 13, wherein:
   said second blade member fixedly engaged to said clevis means includes a lateral protrusion extending from a proximal portion of said fixedly engaged second blade member, said lateral protrusion for engagement with a hole in said clevis means.

15. A surgical hook scissors according to claim 10, wherein:
   said second blade member has a third through-hole in a proximal portion of said second blade member for pivotally engaging said clevis means,
   said rod means is coupled to said pivotally engaged second blade member, and
   when said actuating means imparts reciprocal motion to said rod relative to said tube, said reciprocal motion is translated into pivotal motion of said pivotally engaged second blade member.

16. A surgical hook scissors according to claim 11, wherein:
   said pivotally engaging second blade member has a fourth through-hole in said proximal portion of said second blade member, and said surgical hook scissors further comprises,
   a second connecting means extending through said fourth through-hole and coupling said first end of said rod with said pivotally engaging second blade member.

* * * * *